(12) United States Patent
Meng et al.

(10) Patent No.: US 9,301,942 B2
(45) Date of Patent: Apr. 5, 2016

(54) USE OF ICARITIN FOR THE PREPARATION OF COMPOSITION FOR TREATING CANCER

(71) Applicant: BEIJING SHENOGEN PHARMA GROUP LTD., Beijing (CN)

(72) Inventors: Kun Meng, Beijing (CN); Hongxia Ding, Beijing (CN); Shu Li, Beijing (CN); Ya Tuo, Beijing (CN); Yueqiu Shen, Beijing (CN)

(73) Assignee: BEIJING SHENOGEN PHARMA GROUP LTD., Beijing (CN)

( * ) Notice: Subject to any disclaimer, the term of this patent is extended or adjusted under 35 U.S.C. 154(b) by 0 days.

(21) Appl. No.: 14/291,639

(22) Filed: May 30, 2014

(65) Prior Publication Data

US 2014/0357876 A1 Dec. 4, 2014

(30) Foreign Application Priority Data

May 31, 2013 (CN) .......................... 2013 1 0210669

(51) Int. Cl.
*A61K 31/352* (2006.01)
(52) U.S. Cl.
CPC .................................... *A61K 31/352* (2013.01)
(58) Field of Classification Search
CPC .................................................. A61K 31/352
See application file for complete search history.

(56) References Cited

U.S. PATENT DOCUMENTS

2008/0146658 A1* 6/2008 Li et al. .......................... 514/456
2008/0214844 A1 9/2008 Zhang et al.

FOREIGN PATENT DOCUMENTS

| CN | 101302548 A | 11/2008 |
|---|---|---|
| CN | 101528038 A | 9/2009 |
| EP | 2660240 A1 | 11/2013 |
| WO | 2008052005 A2 | 5/2008 |

OTHER PUBLICATIONS

Clinical Trials Icaritin (http://clinicaltrials.gov/ct2/show/NCT01278810) (PD:Jan. 18, 2011).*
Cancer definition in MedicineNet.com-2004.*
Scholz, et al., "Interactions Affecting the Bioavailability of Dietary Polyphenols in Vivo"; Int. J. Vitam. Nutr. Res. 77(3), 2007, pp. 224-235.
Tiong, et al.; "A Novel Prenylflavone Restricts Breast Cancer Cell Growth Through AhR-mediated destabilization of ERα Protein"; Carcinogenesis, vol. 33, No. 5, pp. 1089-1097, 2012.
Guo, et al., "An Anticancer Agent Icaritin Induces Sustained Activation of the Extracellular Signal-regulated Kinase (ERK) Pathway and Inhibits Growth of Breast Cancer Cells"; European Journal of Pharmacology 658 (2011) pp. 114-122.

(Continued)

*Primary Examiner* — Valerie Rodriguez-Garcia
(74) *Attorney, Agent, or Firm* — Scully, Scott, Murphy & Presser, P.C.

(57) ABSTRACT

The present invention provides the use of Icaritin for the preparation of a composition for treating cancer, wherein the composition is orally administered to a patient at least one cycle, each cycle comprising a continuous 28-day dosing schedule, in which Icaritin is administered at least once daily, at a dosage of 400-1800 mg daily. The patients treated with Icaritin according to the present method receive better treatment, with reduced adverse effects.

4 Claims, 5 Drawing Sheets

(56) References Cited

OTHER PUBLICATIONS

Zhu, et al., "Icaritin Shows Potent Ani-Leukemia Activity on Chronic Myeloid Leukemia in Vitro and in Vivo by Regulating MAPK/ERK/JNK and JAK2/STAT3/AKT Signalings"; PLoS One 6(8): Aug. 2011; e23720.

Chang, et al., "Oral Absorption and Excretion of Icaritin, an Aglycone and also active Metabolite of Prenylflavonoids from the Chinese Medicine Herba Epimedii in Rats"; Phytomedicine 19 (2012), pp. 1024-1028.

He, et al., "Incaritin Induces Apoptosis of HepG2 Cells Via the JNK1 Signaling Pathway Independent of the Estrogen Receptor"; Plant Med 2010; 76: pp. 1834-1839.

The Phase II Study of Icaritin in Patients With Advanced Hepatocellular Carinoma. (2013). Retrieved from http://clinicaltrials.gov/show/NCT01972 (Identification No. NCT01972672).

Phase I Study of Novel Estrogen Receptor (ER) a36 Modifier Icaritin in Advanced Breast Cancer Patients. (2011). Retrived from http://clinicaltrials.gov/show/NCT01278810 (Identification No. NCT01278810).

Database EMBASE [Online]; Elsevier Science Publishers, Amsterdam, NL; Mar. 2012.

European Serch Report dated Oct. 10, 2014 directed to corresponding European Patent Appln. No. EP 14 17 0515.

* cited by examiner

USE OF ICARITIN FOR THE PREPARATION OF COMPOSITION FOR TREATING CANCER

TECHNICAL FIELD

The present invention is related to the use of Icaritin for the preparation of a composition for treating cancer.

BACKGROUND OF THE INVENTION

ER-α36 is a recently discovered estrogen receptor, predominantly located on the plasma membrane and in the cytoplasm, that is found to mediate membrane-initiated "non-genomic" signaling pathways. The membrane-initiated signal has been acknowledged as a fast response signal related to estrogen, and usually activates the signaling pathway such as MAPK/ERK, phosphatidylinositol 3-kinase and protein kinase C. Pre-clinical experiments disclose that ER-α36 expression in tumor cells appears to drive the propagation of breast cancer cells. Further, ER-α36 has been found to be expressed in many cancers, and plays an important role in cancer and tumor progression.

Icaritin, referring to the formula (I), is a new and effective monomer obtained by the enzyme hydrolysis of Icariin, which is an active ingredient isolated from Epimedium Herb.

(I)

Icaritin is disclosed in China patent ZL.200780039276.9 for the treatment of diseases related to the abnormal proliferation of estrogen receptor cells expressing ER-α36, wherein the diseases comprise several varieties of cancers.

The method of preparing Icaritin is disclosed in CN101302548B. In this method, Icariin, as a starting material, is hydrolyzed with β-D-Glucosidase, centrifuged, and the pellet obtained from centrifugating the hydrolysis product is dissolved with acetone. Following a second centrifugation and filtration, the supernatant is collected. Pure Icaritin is obtained after recrystalizing the supernatant.

There is no report about administrating Icaritin to a subject in the prior art.

SUMMARY OF THE INVENTION

The present invention is directed to the use of Icaritin for the preparation of a composition for the treatment of cancer.

In one aspect, the present invention provides the use of Icaritin for the preparation of a composition for treating cancer, wherein the composition is orally administered to a patient for at least one cycle, each cycle comprising a continuous 28-day dosing schedule, in which Icaritin is administered at least once daily, at a dosage of 400-1800 mg daily.

Preferably, the composition is orally administered to the patient after meal.

Preferably, the dosage of Icaritin is a 600-1600 mg twice daily.

Preferably, the dosage of Icaritin is a 800-1600 mg twice daily.

Preferably, the dosage of Icaritin is a 1200-1600 mg twice daily.

Preferably, the dosage of Icaritin is a 600-800 mg twice daily.

Preferably, the dosage of Icaritin is a 600 mg thrice daily.

Preferably, the composition is administered to the patient for at least 2 cycles.

The advantage of the present invention is the inventors' discovery of the best pattern for administrating Icaritin to a patient for cancer treatment. The inventors have found that the present administration methods have improved efficacy with reduced side-effects.

DETAILED DESCRIPTION OF THE INVENTION

Definitions

Figure 1:
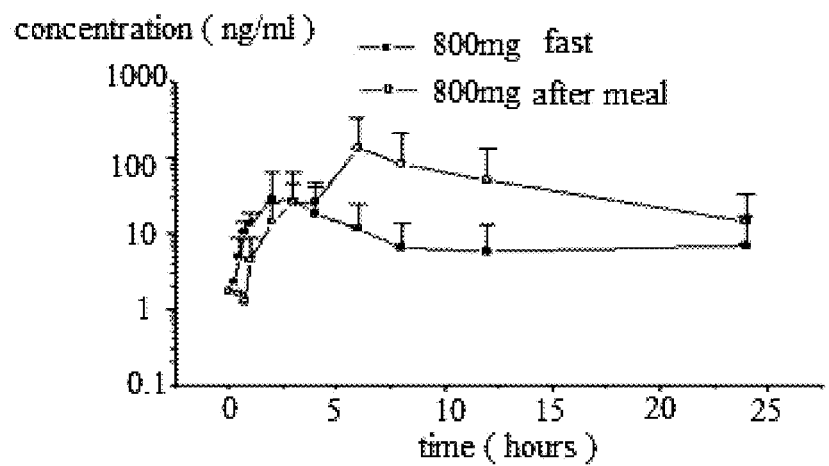
FIG. 1 demonstrates the pharmacokinetics of Icaritin administered 800 mg once daily respectively before or after meals.

As used herein, the following terms have the meanings given below:

"Subjects" or "Patients" refers to mammals, including but not limited to humans, suffering from cancers.

"Maximum Tolerated Dose (MTD)" means the highest dose of a radiological or pharmacological treatment that will produce the desired effect without unacceptable toxicity. In the present invention, MTD is one dose level below the cohort in which 2 patients experienced a drug-related dose limited toxicity in cycle 1.

"CR" means a complete response was achieved after treatment, that is, all signs of cancer in the patient disappeared in response to the treatment.

"PR" means a partial response was achieved after treatment, that is, at the end of treatment, there was some disease remaining but a reduction of disease by 30% or more on clinical examination or x-rays and scans was achieved in the patient.

"SD" means a stable disease state was seen, that is, at the end of the treatment, the disease state of the patient was little changed from pre-treatment conditions.

"PD" means a progressive disease state was seen, that is, the disease shows more than a slight increase in size or extent on or after treatment.

"OS" means overall survival days of patients. Overall survival is an indication of the proportion of people within a group who are expected to be alive after a specified time, taking into account death due to any cause, both related and unrelated to the cancer in question.

"TTP" means time to progression in the patients, that is, the length of time from the date of diagnosis or the start of treatment for a disease until the disease starts to get worse or spread to other parts of the body. In a clinical trial, measuring the time to progression is one way to see how well a new treatment works.

EXAMPLES

The following examples are provided to illustrate the invention and are not intended to limit the invention. Any amendments or changes are within the scope of the present invention.

I. Study Design

1. Phases of the Study

The clinical trial includes two phases: Phase I aims to seek the maximum tolerated dose in the patients. Phase II aims to obtain the administration dosage to the patient treatments.

1.1 Phase 1a: Dose-escalating study with patients suffering from advanced breast cancer. Cohorts of 3-6 patients received one dose, and 6 planned doses of 50, 100, 200, 400, 800, 1600 mg/day were orally administered to the patients over at least a 28-day cycle.

1.2 Phase 1b: Fixed doses of Icaritin with 600 mg and 800 mg BID (Bis in diem) were administered to patients suffering from advanced solid tumors for at least a 28 day cycle.

2. Major Inclusion Criteria

Phase Ia: Females of age≥18 years old and ≤65 years old, suffering from advanced breast cancer which was not responsive to previous standard treatments, were selected based on Eastern Cooperative Oncology Group (ECOG) score≤1.

Phase Ib: Advanced cancer patients without standard treatment, especially HCC patients with Child-Pugh Class A or B liver function, were selected.

3. Major Exclusion Criteria

Phase Ib: Patients with the following conditions were excluded: ECOG score≥2, ANC≤1500 cells/μL, platelet≤80,000 cells/μL, Hb≤9.0 g/dL, bilirubin>1.5×ULN, AST or ALT>5×ULN, or albumin<2.8 g/dL.

The patients with the following conditions were also excluded: prior systemic chemotherapy, chemoembolization, percutaneous ethanol injection, or surgery for HCC<30 days.

II. Treatment Cycles Phase Ia

1. Patient Demographics Phase Ia

| | N = 24 mean age 47 (33-62 years old) dose (mg/d) | | | | | |
|---|---|---|---|---|---|---|
| | 50 (n = 3) | 100 (n = 6) | 200 (n = 6) | 400 (n = 3) | 800 (n = 3) | 1600 (n = 3) |
| ER/PR+ | 2 | 5 | 4 | 1 | 1 | 3 |
| HER2+ | 2 | 1 | 2 | 2 | 0 | 0 |
| TNBC | 0 | 1 | 0 | 0 | 2 | 0 |
| Adjuvant chemo | 2 | 6 | 6 | 2 | 1 | 3 |
| Adjuvant endo | 1 | 3 | 2 | 2 | 1 | 2 |
| Visceral mets | 1 | 4 | 6 | 3 | 1 | 2 |
| ≥2 lines of chemo | 1 | 6 | 5 | 2 | 1 | 3 |
| ≥2 lines of endo | 0 | 5 | 5 | 0 | 0 | 2 |

2. Treatment Cycles (28 Days per Cycle)

| | Numbers of patients (n = 24) mean age 47 (33-62 years old) | | | |
|---|---|---|---|---|
| dose (mg/d) | 1 cycle | 2 cycles | 3 cycles | 4 cycles |
| 50 | 1 | 0 | 1 | 1 |
| 100 | 4 | 1 | 1 | 0 |
| 200 | 5 | 0 | 0 | 1 |
| 400 | 2 | 1 | 0 | 0 |
| 800 | 3 | 0 | 0 | 0 |
| 1600 | 3 | 0 | 0 | 0 |
| Total patients | 18 (75%) | 2 (8.3%) | 2 (8.3%) | 2 (8.3%) |

Tumor assessment was performed every 28 days. No CR or PR was observed. Further, 1 patient completed 9 cycles.

3. Adverse Events of Phase Ia

| | Numbers of patients (n = 24*) | | | |
|---|---|---|---|---|
| Adverse events | G1 | G2 | ≥G3/4 | Total (%) |
| Hematological | | | | |
| Leukopenia | 2 | 0 | 0 | 2(8.3) |
| Neutropenia | 4 | 0 | 0 | 4(16.7) |
| anemia | 2 | 0 | 0 | 2(8.3) |
| Laboratory abnormality | | | | |
| ALT/AST increase | 3 | 0 | 0 | 3(12.5) |
| hypercholesteremia | 2 | 0 | 0 | 2(8.3) |
| hematuria | 2 | 0 | 0 | 2(8.3) |
| Constitutional symptoms | | | | |
| Fatigue | 2 | 0 | 0 | 2(8.3) |
| sweat | 2 | 0 | 0 | 2(8.3) |

No G3/4 adverse events were observed. Other unlisted adverse events including myalgia, arthralgia, hypertriglyceridemia, hot flashes, anorexia, rash, and vaginal bleeding, all occurred only in 1 patient.

4. Pharmacokinetics

As seen in FIG. 1, the plasma concentration of 800 mg Icaritin after a meal is higher than the fasting plasma concentration of 800 mg Icaritin.

Figure 2:
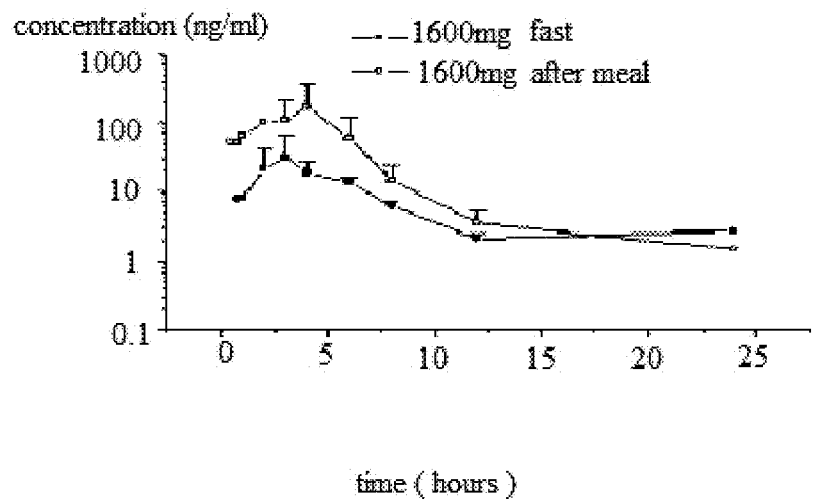
FIG. 2 demonstrates the pharmacokinetics of Icaritin administered 1600 mg once daily respectively before and after meal.

As seen in FIG. 2, the plasma concentration of 1600 mg after a meal is higher than the fasting plasma concentration of 1600 mg Icaritin.

Therefore, bioavailability is better with post-meal dosing than fasting dosing.

Figure 3:
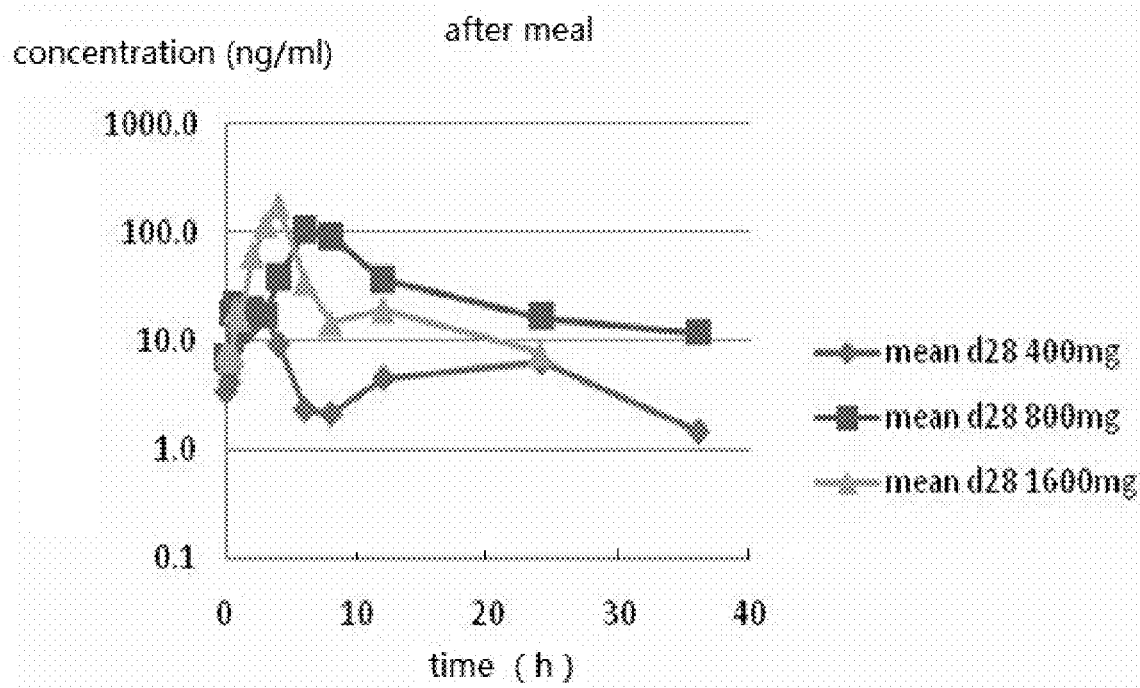
FIG. 3 demonstrates the pharmacokinetics of Icaritin administered 400, 800 and 1600 mg once daily after meal.

As seen in FIG. 3, with dosages of 400 mg, 800 mg and 1600 mg Icaritin, the plasma concentration of Icaritin increases with dose but not in a completely linear pattern. The maximum plasma concentration achieved by 800 mg Icaritin is close to the plasma concentration of 1600 mg Icaritin. In addition, absorption saturation occurs with administration of 1600 mg Icaritin.

This study identifies the half lives of 800 mg and 1600 mg Icaritin BID as respectively 4.8±2.7 h and 4.5±0.8 h. Therefore, Icaritin can be orally administered twice or thrice daily. For patient convenience, Icaritin can be administered twice daily in the Ib phase.

III. Study of HCC Patients in Phase Ib

1. Patient Demographics-Phase Ib HCC Patients

| | N = 18* | |
|---|---|---|
| Dose (mg/d) | 600 mg BID (n = 12) | 800 mg BID (n = 6) |
| Average age | 60(32-73) | 46(33-73) |
| Gender: Male/Female | 10/2 | 5/1 |
| (ECOG 0-1/2) | 11/1 | 6/0 |
| HBC infection | 10 | 6 |
| HCV infection | 1 | 0 |
| Liver cirrhosis | 8 | 6 |
| Child-Pugh A | 10 | 5 |
| Extrahepatic spread,lung/lymph nodes | 4/8 | 3/7 |
| Portal vein tumor thrombus | 5 | 2 |
| operations | 3 | 3 |
| TACE/RFA | 10 | 3 |
| AFP > ULN | 11 | 6 |

2 MBC (metastatic breast cancer) patients, 2 CRC (colorectal cancer) patients, 3 ICC (intrahepatic cholangiocarcinoma) patients, 1 lung cancer patient and 2 clinically diagnosed HCC patients were also enrolled in this phase Ib stage.

2. Serious Adverse Events—Phase Ib

| Serious adverse events | No | dose | relationship | outcomes |
|---|---|---|---|---|
| GI bleeding | 2 | 600/800 | Not related | resolved/death |
| Dyspnea | 2 | 600 | Not related | Death |
| Sepsis | 1 | 800 | Not related | resolved |
| Liver abscess | 1 | 600 | Not related | unresolved |
| epilepsy | 1 | 600 | Not related | unresolved |
| Cardiac sudden death | 1 | 600 | Unlikely related | death |

It can be seen from the demographic that no G2 drug-related adverse events was observed. The drug related toxicity profile was similar to phase Ia, and only one serious adverse effect of pneumonia was observed during study, which was not considered drug-related.

3. Efficacy of HCC Patients—Phase Ib

| | Best response* | | | On-study treatment cycles | | | Off-study extension cycles |
|---|---|---|---|---|---|---|---|
| dose | PR | SD | PD | ≤2 | 3-4 | ≥4# | ≥3& |
| 600 mg bid (n = 12) | 1 (10%) | 5 (50%) | 4 (40%) | 7 (58.3%) | 0 | 5 (41.7%) | 3 |
| 800 mg bid (n = 5) | 0 | 0 | 3 (60%) | 5 (100%) | 0 | 0 | 0 |

One cycle was 28 days and tumor assessment was performed every 2 cycles.

*means based on evaluable patients.

means one HCC patient received 12 months of Icaritin before PD and continued with off-study extension treatment for another 3 months prior to death by cardiac arrest.

&means 3 patients continued with off-study extension treatment for more than 3 months.

Figure 4A:
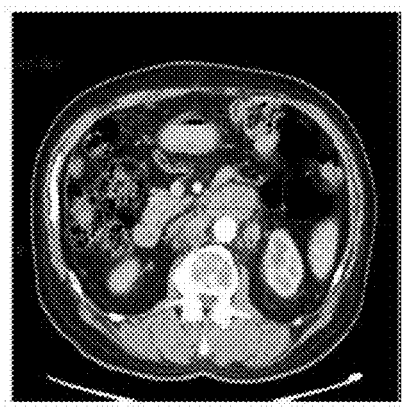
FIG. 4a demonstrates a B-mode ultrasound image of an HCC patient before treatment.
Figure 4B:
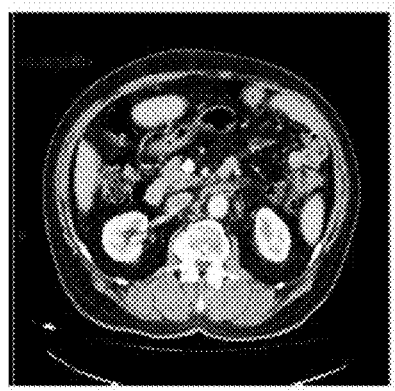
FIG. 4b demonstrates a B-mode ultrasound image of the HCC patient after treatment, showing complete disappearance of abdominal lymph nodes after eight months of treatment.

FIG. 4a demonstrates a B-mode ultrasound image of an HCC patient before treatment and FIG. 4b demonstrates a B-mode ultrasound image of the HCC patient after treatment, showing complete disappearance of abdominal lymph nodes after eight months of treatment.

Figure 5:
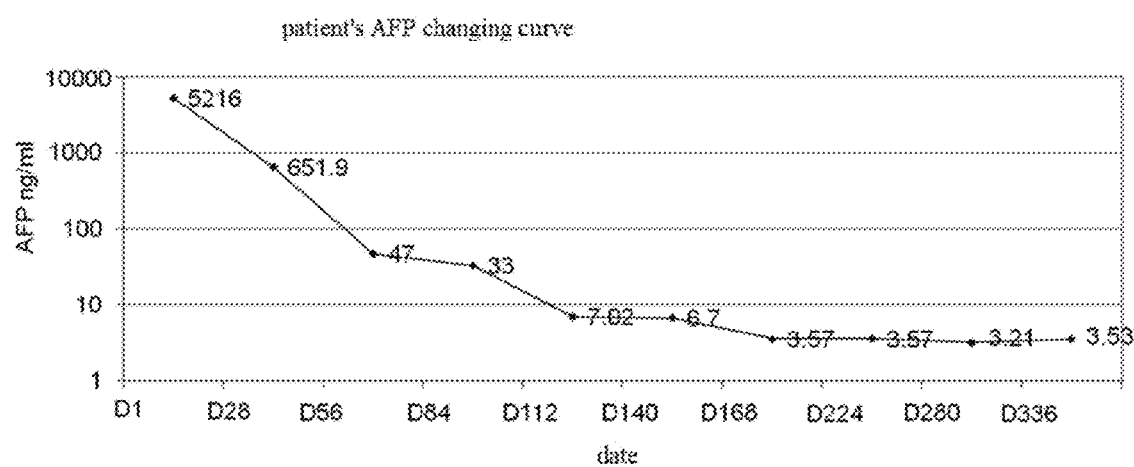
FIG. 5 demonstrates the AFP changing curve of HCC patient in the examples.

FIG. 5 demonstrates that the patient AFP decreases from 5216 ng/ml to 3.53 ng/ml as treatment progressed.

4. Survival of HCC Patients in Phase Ib

Figure 6:
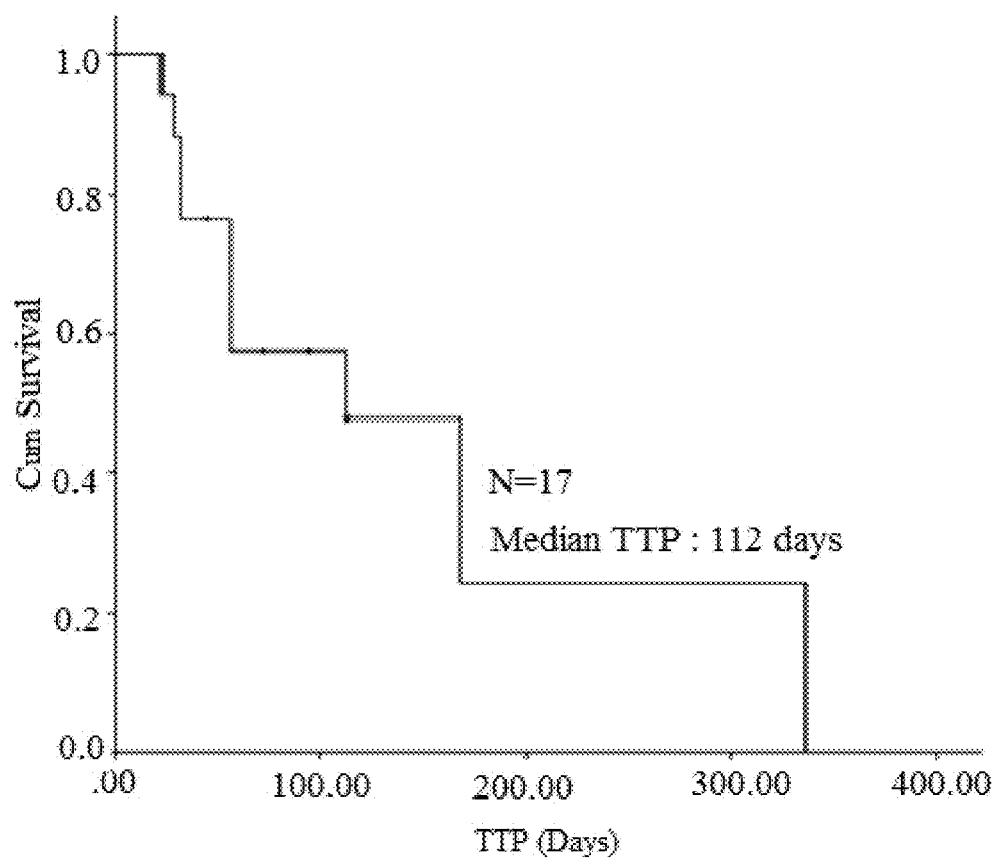
FIG. 6 demonstrates the time to progression of HCC patients in the examples.
Figure 7:
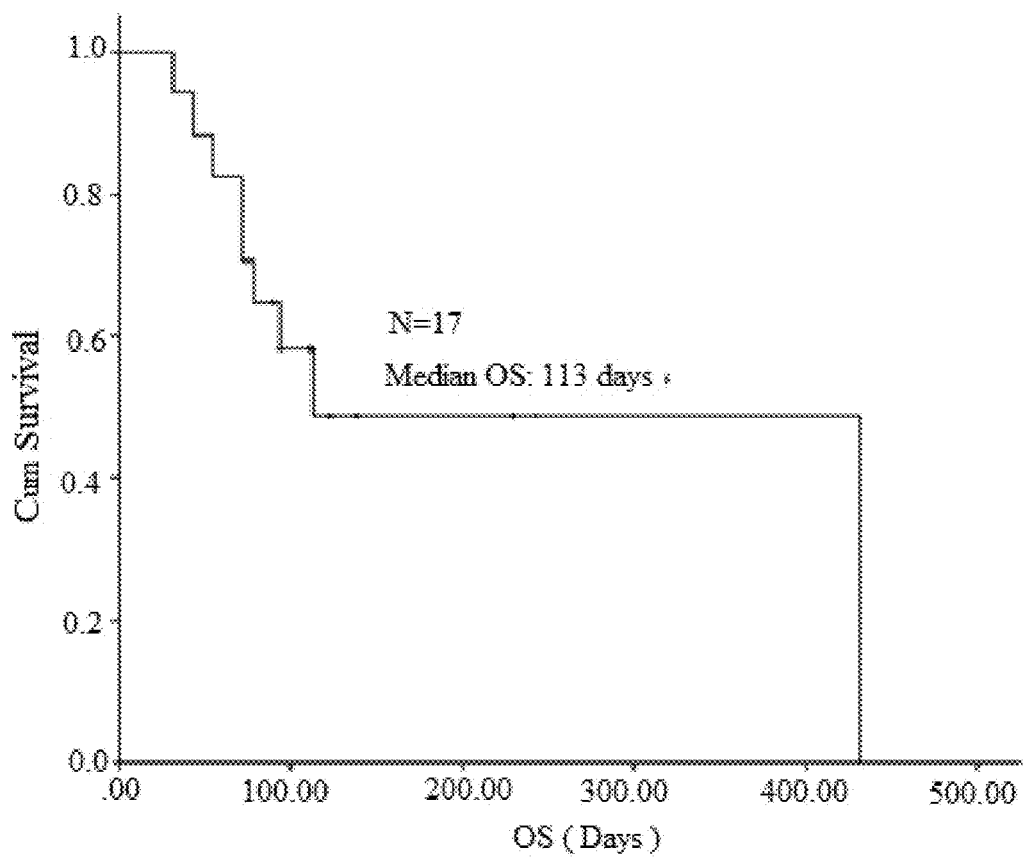
FIG. 7 demonstrates the overall survival of HCC patients in the examples.

As seen in FIG. 6, the median TTP of HCC patients was 112. Referring to FIG. 7, one patient was just recruited into the study, so 17 patients were analyzed for survival. FIG. 7 shows that the median OS was 113 days (95% CI:32-265).

In all, Icaritin up to 1600 mg/d was well tolerated in patients with advanced malignancies, and no dose tolerated toxicity was found in this phase of clinical trial.

Pharmacokinetics results show better bioavailability in fed dosing.

Icaritin shows potential anti-tumor effect in advanced breast cancer and promising efficacy in hepatocellular cancer.

The invention claimed is:

1. A method of treating cancer in a patient, comprising orally administering icaritin to the patient for at least one cycle, wherein each cycle comprises a continuous 28-day dosing schedule, and wherein said icaritin is administered at least twice daily, at a total daily dosage of 800-1600 mg, wherein said icaritin is orally administered to the patient after meal, and wherein said cancer is selected from breast and hepatocellular cancer.

2. The method of claim 1, wherein the icaritin is administered twice daily, at a total daily dosage of 1200-1600 mg.

3. The method of claim 1, wherein the icaritin is administered to the patient for at least 2 cycles.

4. The method of claim 1, wherein said cancer hepatocellular cancer.

* * * * *